United States Patent [19]

Graziello

[11] Patent Number: 4,874,895

[45] Date of Patent: Oct. 17, 1989

[54] PROCESS FOR PURIFYING CRUDE TRIFLURALIN

[75] Inventor: Donadello Graziello, Valdagno, Italy

[73] Assignee: Finchimica S.p.A., Manerbio, Italy

[21] Appl. No.: 313,356

[22] Filed: Feb. 17, 1989

Related U.S. Application Data

[63] Continuation of Ser. No. 129,347, Nov. 27, 1987, abandoned, which is a continuation of Ser. No. 824,888, Jan. 31, 1986, abandoned.

[30] Foreign Application Priority Data

Dec. 18, 1985 [IT] Italy .............................. 23247 A/85

[51] Int. Cl.$^4$ .................... C07C 85/26; C07C 111/00; C07C 85/11; C07C 87/60
[52] U.S. Cl. .................................... 564/437; 564/112; 564/414; 564/441
[58] Field of Search ................. 564/112, 414, 437, 441

[56] References Cited

U.S. PATENT DOCUMENTS

| | | | |
|---|---|---|---|
| 3,317,607 | 5/1967 | Latourette et al. | 564/465 |
| 3,586,719 | 6/1971 | Bil | 564/441 |
| 3,927,127 | 12/1975 | Damiano | 564/441 |
| 4,120,905 | 10/1978 | Cannon et al. | 564/437 |
| 4,127,610 | 11/1978 | Eizember | 564/437 |
| 4,134,917 | 1/1979 | Ross et al. | 564/437 |
| 4,136,117 | 1/1979 | Diehl et al. | 564/414 |
| 4,185,035 | 1/1980 | Eizember et al. | 564/437 |
| 4,226,789 | 10/1980 | Eizember et al. | 564/437 |
| 4,338,473 | 7/1982 | Habig et al. | 568/933 |
| 4,440,962 | 4/1984 | Palluca | 568/933 |
| 4,501,608 | 2/1985 | Cannon | 71/121 |
| 4,537,992 | 8/1985 | Pikarski et al. | 564/437 |

OTHER PUBLICATIONS

Overberger, et al., *Organic Compounds with Nitrogen–Nitrogen Bonds*, (1966), pp. 83–98.
Wallis, "Preparation of Pure Piperidine", *Lieb. Ann.*, 345:277 (1906).
Biggs, et al., "Kinetics and Mechanism of the Fischer–Hepps Rearrangement and Denitrosation. Part V. The Mechanism of Denitrosation", *J. Chem. Soc. Perkins II*, p. 107, (1975).
Fridman, et al., "Advances in the Chemistry of Aliphatic N-Nitrosamines", *Russian Chemical Review*, 40(1):34–50 (1971).
Eisenbrand, et al., *Arneimittel-Forschung*, 20(10):1513–1517.
Helvetica Chimica Acta, 47:166 (1964).
Probst, "Reduction of Nitrosamine Impurities in Pesticide Formulations", 181$^{st}$ Meeting of ACS, Mar. 31–Apr. 1, 1981, pp. 363–382.
Johnson et al., "The Specificity of the Release of Nitrite from N-Nitrosamines by Hydrobromic Acid", *Analytical Letters*, 4(6):383–386 (1971).
Eizember, R. F. et al., "Destruction of Nitrosamines. Treatment of Nitrosamines with Various Acids and Halogens", *J. Org. Chem.*, vol. 44, No. 5, pp. 784–786 (1979).

*Primary Examiner*—Richard L. Raymond
*Assistant Examiner*—Peter G. O'Sullivan
*Attorney, Agent, or Firm*—Bernard, Rothwell & Brown

[57] ABSTRACT

The level of the nitrosamines which may be present in the unrefined trifluralin is reduced to a value below 0.5 ppm, by treating the unrefined trifluralin under agitation, at a temperature from 60° to 90° C., for a time between 10 minutes and 4 hours, with an aqueous solution containing from 15 to 50% by weight of hydrobromic acid in a ratio of 0.2 to 0.8 liters per kilogram of unrefined trifluralin, said aqueous solution of hydrobromic acid being added with an amount of sulfamic acid from 0.1 to 3 g per liter of solution and with an amount of bisulfite or an alkali metal corresponding to a content of sulphur dioxide from 0.3 to 1.2 g per liter of said hydrobromic acid aqueous solution.

The so obtained refined trifluralin has a content of nitrosamines which is lower than 0.1 ppm.

8 Claims, No Drawings

PROCESS FOR PURIFYING CRUDE TRIFLURALIN

This is a continuation of application Ser. No. 129,347, filed Nov. 30, 1987, which is a continuation of Ser. No. 824,888, filed Jan. 31, 1986.

The present invention relates to an improved process of purifying crude trifluralin containing trace amounts of nitrosamines, in order to reduce the level thereof to a value below at least 0.5 ppm.

Trifluralin is the commercial name for 4-trifluoromethyl-2,6-dinitro-N,N-di-n-propylaniline, which is widely used in agriculture as a herbicide.

Following the development of highly sensitive methods of analysis, e.g. those using mass-spectrography of eluates of chromatographic separation (GC/MS), it was verified that some unrefined trifluralin contained nitrosamines in small quantities, typically from a few ppm to a few hundred ppm.

The origin of nitrosamines in trifluralin can derive from the final stage of the conventional preparation process which consists of a reaction between di-n-propylamine and 4-trifluoromethyl-2,6-dinitro-chloro-benzene according to the equation (I):

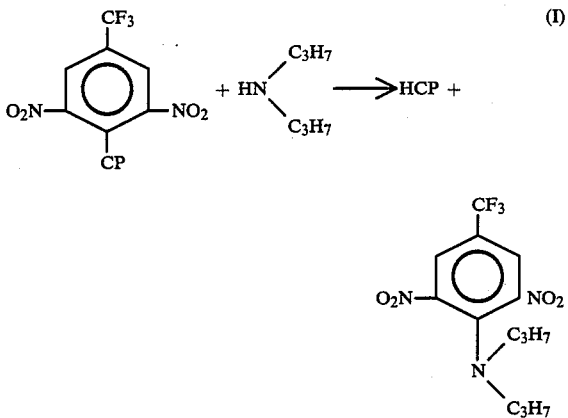

The compound 4-trifluoromethyl-2,6-dinitro-chloro-benzene may contain some nitrosating agents which react with the amine to form the nitrosamine.

The presence of nitrosamines in trifluralin, even in quantities of a few ppm is considered undesirable due to the discovery of carcinogenic properties of some nitrosamines in animals.

In order to prepare a refined trifluralin, with a nitrosamine content lower than 0.5 ppm, which at present is the level commercially desirable, several processes have been developed either by preventing the formation of nitrosamines by previously treating the dinitro derivative to remove therefrom the nitrosating agents which could give rise to the formation of nitrosamines, or by removing the nitrosamines from trifluralin.

Among the processes for the elimination of the nitrosating agents from the dinitro derivative used as an intermediate in the preparation of trifluralin, are those disclosed by U.S. Pat. Nos. 4,120,905 and 4,338,473, which are based on the treatment of said intermediate with an aqueous solution of alkaline substances and the simultaneous bubbling through said solution of an inert gas or, simply, with water, which is at least partially removed by distillation.

These processes cannot however guarantee the complete removal of the nitrosating agents, since no analytical methods for these exist so that the certainty of their removal can only be verified after the preparation of the final trifluralin product and analysis of its nitrosamine content.

In order to remove the nitrosamines from the final product it was disclosed to treat trifluralin with a concentrated aqueous solution of hydrochloric acid or with gaseous hydrochloric acid (U.S. Pat. No. 4,226,789) or with inorganic acid chlorides (U.S. Pat. No. 4,185,035) or with chlorine or bromine (U.S. Pat. No. 4,127,610).

Although all these processes have been proven to be effective to cause the destruction of the nitrosamines, they are not free from drawbacks mainly due to the long reaction time required to reduce the nitrosamine content to a level below at least 0.5 ppm.

Furthermore, it was found that the treatment of trifluralin with hydrochloric acid causes the formation of di-n-propylamine and 4-trifluoromethyl-2,6-dinitro-chloro-benzene, due to the reversal of the above mentioned reaction (I), whereby the hydrochloric aqueous phase and likely also the organic phase are contaminated with amines.

This originates a twofold drawback. On the one hand, in order to allow the optional recycle of the hydrochloric acid solution, the latter must be thoroughly purified, on the other hand, even the trace amount of amines contained in the trifluralin phase may—by reaction with nitrogen oxides which are present in the atmosphere—cause the formation of nitrosamines during the further processing of trifluralin to obtain herbicidal compositions.

It is also to be noted that in order to achieve a sufficiently fast reaction rate, the hydrochloric acid solution is generally used with a concentration higher than 20% wt, typically 35% wt, so that the required distillation of the used solution leads to obtain an azeotropic mixture with a 20% wt HCl concentration, which can hardly be re-used.

It is also known that the destruction of the nitrosamines contained in the trifluralin may be carried out by treatment with an aqueous hydrobromic acid solution, as disclosed e.g. by R. F. Eizember et Al., Journal of Organic Chemistry vol. 44 (1979), pages 784–786, however the use of hydrobromic acid never found industrial application up to now. In fact, in spite of the fact that the rate at which the nitrosamines are destroyed by the hydrobromic acid is much higher than that with hydrochloric acid when one uses an aqueous solution of acid that has not been used before for the same purpose, it diminishes rapidly when the same solution is re-used. A reduction in the destructive activity is furthermore observed, so much so that after only a few recyclings of the solution, the content of nitrosamines cannot be reduced below levels of 1 ppm, no matter how long the time or how high the temperature of the treatment are.

There is a kind of "poisoning" of the aqueous solution of hydrobromic acid which makes its further use practically impossible. Furthermore, strong difficulties have been encountered to transfer from the laboratory scale, wherein the treatment with hydrobromic acid is effected with hydrobromic acid of analytical grade, to the industrial scale wherein it is necessary to use hydrobromic acid of technical grade. In fact, while the reaction leading to the destruction of the nitrosamines proceeds rapidly with freshly prepared hydrobromic acid of analytical grade, the same reaction occurs with difficulty with hydrobromic acid of technical grade, likely because of the presence in it of not well identified impurities which hinder the kinetics.

In fact, in the patent literature, processes which make use of hydrochloric acid alone have been disclosed, while the use of hydrobromic acid is recited exclusively in combination with other substances, e.g. aldehydes and ketones such as mentioned in U.S. Pat. No. 4,134,917.

It has now been found, and this constitutes the basis of the present invention, that it is possible to completely eliminate the poisoning of the aqueous hydrobromic acid solutions which are used in the treatment of crude trifluralin containing nitrosamines and to use in this treatment hydrobromic acid of technical grade if small quantities of sulfamic acid and of alkali metal bisulfite are added to the hydrobromic acid solution.

Accordingly, the object of the present invention is to provide an improved process of purifying crude trifluralin containing nitrosamines to reduce the level thereof to a value below at least 0.5 ppm, comprising mixing the trifluralin under agitation with an aqueous solution of hydrobromic acid, characterised in that it further comprises the step of adding to said aqueous hydrobromic acid solution an amount of sulfamic acid of from 0.1 to 3 g per liter of said aqueous solution and an amount of alkali metal bisulphite corresponding to a content of $SO_2$ from 0.3 to 1,2 g per liter of said aqueous solution.

The process according to the present invention makes the use of aqueous hydrobromic acid solutions industrially convenient with respect to the conventional processes, since it is possible to use solutions of technical grade and furthermore it allows several recyclings of the solution, apart from the need of making up the quantity of hydrobromic acid which reacts with the nitrosamines present in the unrefined trifluralin.

The mechanism of action of sulfamic acid on the aqueous solution of hydrobromic acid was not very clear, but it is thought that it destroys nitrosylic type compounds which form during the treatment of the unrefined trifluralin and which are able to regenerate the nitrosamines by reaction with the trifluralin. As to the mechanism of action of the alkali metal bisulphite, it is thought that sulphur dioxide deriving therefrom act as a reducing agent to cause the chemical reduction of nitro compounds to nitroso compounds which in turn may be destroyed by the action of hydrobromic acid and sulfamic acid.

Typically the treatment with the aqueous hydrobromic acid solution is carried out at a temperature from 20° to 90° C., preferably between 60° and 90° C. The reaction time typically ranges from 10 minutes to 4 hours, a reaction time of about 30 minutes being sufficient to achieve a reduction of the nitrosamine level to below 0.5 ppm when the reaction is carried out at 80° C.

The concentration of hydrobromic acid in the aqueous solution used for the process according to the invention is not particularly critical relative to the destruction of the nitrosamines; it is however necessary to avoid having aqueous solutions with the same density as that the molten trifluralin to avoid useless complications in the separation of the trifluralin from the acid aqueous solution at the end of the treatment. Typically, the aqueous hydrobromic acid solution has a concentration of hydrobromic acid between 15 and 50% by weight, preferably between 23% and 27% by weight.

The latter concentration range is preferred as to the more flavorable kinetics, the greater ease of separation between the aqueous and the trifluralin phases at the end of the treatment and as to the possibility of further recycling of the solution when it has been used for several recyclings and needs be regenerated by distillation. In fact, the distillation of an aqueous solution having a concentration of hydrobromic acid within the above-mentioned preferred range yields an azetropic mixture having a concentration of hydrobromic acid of 48% wt which may be easily re-used in the process by being diluted to 25% wt and by addition of fresh hydrobromic acid.

The ratio of the aqueous solution of hydrobromic acid and the trifluralin to be treated is not particularly critical and is typically between 0.2 and 0.8 liters of aqueous acid solution of per kilogram of trifluralin.

Greater volumes of solution show no improvement in the results, while an excessively low value of said ratio makes contact more difficult between the two liquid phases during the treatment.

In the preferred embodiments of the invention, ratios between the acidic aqueous solution and the trifluralin of from 0.3 to 0.5 liters/kilogram are used.

Typically, the amount of sulfamic acid is from 0.1 to 3 g/liter of acidic solution, preferably from 0.4 to 0.7 g/liter. Smaller quantities of sulphamic acid are insufficient to purify the aqueous solution of hydrobromic acid, while greater quantities show no advantage but increase the cost of the treatment.

As it is known, sulfamic acid is very soluble in water, it is therefore possible to add the desired amount of sulfamic acid directly to the aqueous solution of hydrobromic acid obtaining almost immediate dissolving.

Preferably, aqueous solutions of sulfamic acid with concentrations from 10 to 20% wt are used, since they are more manageable and allow a simpler dosage of the small quantity which has to be used. The reaction rate of sulphamic acid with the impurities which poison the aqueous solution of hydrobromic acid is very fast and it may be considered as terminated by the end of the addition of the sulfamic acid.

As alkali metal bisulfite, it is preferably used sodium bisulfite in a quantity corresponding to a content of sulfur dioxide from 0.3 to 1.2 g/liter of aqueous solution of hydrobromic acid, preferably from 0.5 to 0.8 g/liter of said solution.

Sodium bisulfite may be used in the forms commercially available, such as anhydrous sodium bisulfite having a content of $SO_2$ of about 60% by weight or a solution of sodium bisulfite with a content of $SO_2$ from 24 to 26% by weight or sodium metabisulfite having a content of $SO_2$ of about 65% by weight.

According to the process for the removal of the nitrosamines, the crude trifluralin is mixed under strong agitation with the aqueous solution of hydrobromic acid which has been added with sulfamic acid and sodium bisulfite. The molten organic phase is then separated while still hot from the aqueous solution of hydrobromic acid and the refined trifluralin is recovered from the molten organic phase by washing it—while hot—with slightly alkaline water in order to substantially neutralize the pH and afterwards by solidifying the molten mass by cooling.

The aqueous phase of hydrobromic acid separated from the molten organic phase is then added again with sulfamic acid and bisulfite without letting the temperature decrease below 50° C. and it is then re-used for the treatment of a new batch of trifluralin.

The following examples, which were performed on a laboratory scale as well as on an industrial plant, demonstrated that it is possible to recycle the solution up to twenty times at least, obtaining each time the reduction of the nitrosamine level to a value below 0.5 ppm. The refined trifluralin thus obtained was shown furthermore to be very stable against further formation of nitrosamines during the thermal treatment to which it is subjected during the further processing which is applied to obtain the herbicidal compositions.

The analyses for the determination of the nitrosamines were made in every case with mass spectrometry of eluates chromatographically separated and afterwards concentrated by means of the Kuderna-Danish apparatus.

EXAMPLE 1 (COMPARATIVE)

200 g of trifluralin containing 39.88 ppm of nitrosamines were introduced into a 750 ml glass flask provided with an agitator, thermometer, loading porthole, suction tube, counterflow reflux condensor and immersed in a thermostatic bath. The trifluralin was heated in the flask to 70° C. and then, under agitation, 80 ml of an aqueous solution of hydrobromic acid of analytical grade were added. The treatment was continued for 1 hour, maintaining the temperature and agitation, the agitation was stopped and without cooling, the organic liquid phase (molten trifluralin) was separated from the acidic aqueous solution. The acidic solution was left in the flask and re-used for further treatments of other portions of unrefined trifluralin as described above.

Each batch of the separated trifluralin was analyzed to determine the nitrosamine content. It was observed that the nitrosamine content of the treated trifluralin in the first 10 treatments was always below 0.1 ppm, while after the 10th treatment the value rose rapidly to a value above 1 ppm after the 20th treatment.

No substantial differences in results from those reported were observed by varying the concentration of the hydrobromic acid in the aqueous solution (from 15 to 50% by weight) and the ratio between the volumes of acidic solution and the weight of the crude trifluralin between 0.2 and 0.8 and by raising the temperature of the treatment up to 90° C.

It was possible thus to verify that the nitrosamines could not be completely destroyed by re-using the same solution of hydrobromic acid for more than 10 times.

The same test was repeated using technical grade hydrobromic acid obtaining from different commercial vendors.

While with some kinds of technical hydrobromic acid the test gave results which were equivalent to those obtained with analytical grade hydrobromic acid, with some kinds of technical hydrobromic acid even from the first treatment it was not possible to reduce the level of nitrosamines to below 0.5 ppm, thus showing that the use of technical hydrobromic acid cannot be relied on in the industrial practice.

EXAMPLE 2

1200 kg of an aqueous solution of 25% by weight of technical grade hydrobromic acid (density 1.23) were loaded into a jacketed reactor of 5 m³ capacity, provided with an inner enamel lining, counterflow reflux, loading porthole and with a bottom porthole for discharging the contents. The solution was maintained under agitation at a temperature of 70° C. To said solution 0.5 kg of sulfamic acid and 2.0 liters of a solution of sodium bisulfite with a density of 1.3 corresponding to 0.65 kg of sulfur dioxide were added. Then 3300 kg of molten unrefined trifluralin having a content of nitrosamines of about 39 ppm were loaded into the reactor and the whole mass was kept under agitation at a temperature of 70° C. for 3 hours. The agitation was stopped but the temperature was maintained at 70° C. and the reaction mass was allowed to separate into two liquid phases. The lower phase consisting of molten trifluralin was then discharged through the bottom porthole of the reactor. The trifluralin was washed while hot with a saturated aqueous solution of sodium bicarbonate and then with water and delivered to storage. A sample of treated trifluralin showed a nitrosamine content of less than 0.1 ppm.

0.5 kg sulfamic acid and 2.0 liters of sodium bisulfite were then added into the reactor to the aqueous hydrobromic acid phase. The same results were obtained when the above described process was repeated for more than twenty times. Every five operations the strength of the hydrobromic acid was checked and restored to 25% by weight if necessary by the addition of concentrated hydrobromic acid solution.

EXAMPLE 3

In order to verify the heat stability of the trifluralin treated according to the process described in example 2, against the further formation of nitrosamines, several samples of the thus obtained trifluralin were analyzed after having been subjected to a thermal treatment. The refined trifluralin was stored in metal drums with a capacity of 250 kg, some of which were provided with an enamel inner lining. The drums to be analyzed were randomly chosen and the nitrosamine content was determined by drawing a sample of trifluralin from the drum which had been heated up to a temperature of about 93°–95° C. which is required to obtain trifluralin in the molten state.

In Table I, shown hereinafter, there are indicated the nitrosamine content expressed in ppm, as determined on samples drawn at time 0, that is as soon as heating of the drum has caused full melting of the trifluralin therein contained and after having maintained the trifluralin at a temperature of 93°–95° C. for a time of 24 and 96 hours respectively. The nitrosamine content shown in Table I corresponds to the amount of nitrosodipropylamine (NDPA).

TABLE I

| Lot No. | Enamel Lining | NDPA found (ppm) | | |
|---|---|---|---|---|
| | | Time 0 h | Time 24 h | Time 96 h |
| 186 | N | 0.20 | 0.19 | 0.24 |
| 180 | N | 0.14 | 0.17 | 0.22 |
| 182 | N | 0.20 | 0.38 | 0.59 |
| 188 | Y | 0.05 | 0.19 | 0.03 |
| 189 | Y | 0.41 | 0.45 | 0.65 |
| 196 | Y | 0.05 | 0.18 | 0.21 |
| 196 | Y | 0.07 | 0.09 | 0.11 |
| 192 | Y | 0.14 | 0.23 | 0.32 |
| 194 | Y | 0.05 | 0.05 | 0.05 |
| 194 | Y | 0.1 | 0.1 | 0.1 |
| 198 | Y | 0.2 | 0.35 | 0.32 |
| 198 | Y | 0.35 | 0.40 | 0.38 |
| 202 | Y | 0.23 | 0.33 | 0.36 |

N = drum without enamel inner lining
Y = drum with enamel inner lining

The results of the NDPA analysis show the excellent stability of the product thus obtained, which only in a few cases presents a content of NDPA higher than 0.5 ppm following the most severe heat treatment at 93°–95° C. for 96 hours.

EXAMPLE 4 (COMPARATIVE)

In order to verify the increased stability against nitrosamines formation of the refined trifluralin obtained by the process of the invention, comparative tests were carried out by treating the crude trifluralin by the conventional process consisting of treatment with a hydrochloric acid solution.

The experimental tests were conducted on a laboratory scale by means of a 6 l glass flask provided with agitator, thermometer and reflux condensor. The unrefined trifluralin introduced into said flask was treated with a 30% wt hydrochloric acid solution (10% wt with respect to the trifluralin weight) at 70° C. for 3 hours. Further experiments were carried out by adding to the hydrochloric acid solution 0.250 g sulfamic acid (tests 1a, 1b and 3 in Table II hereinafter). After each treatment, the trifluralin was separated from the hydrochloric acid solution and neutralized with an aqueous solution of sodium bicarbonate. The thus obtained trifluralin was stored in metal containers having a capacity of 0.25 kg, some of which were provided with an enamel lining.

The stability tests were carried out by heating the containers to a temperature in the range of 93°–95° C. and the NDPA content was measured at time 0, and after 24 and 96 hours as described in example 2.

The obtained results are summarized in Table II.

TABLE II

| Test | Enamel lining | Sulfamic acid | NDPA amount (ppm) | | |
|---|---|---|---|---|---|
| | | | Time 0 h | Time 24 h | Time 96 h |
| 1 | N | NO | 0.09 | 0.35 | 1.01 |
| 1a | Y | YES | 0.60 | 1.36 | 2.80 |
| 1b | N | YES | 0.46 | 1.03 | 2.03 |
| 2 | N | NO | 0.44 | 0.98 | 0.96 |
| 3 | N | YES | 0.11 | 0.41 | 1.01 |

By comparing the experimental results of Table II with the results of Table I, it appears that the trifluralin obtained by the process of the present invention presents an increased heat stability against nitrosamine formation particularly under severe heat treatment with respect to the trifluralin obtained by the conventional processes.

It is believed that the advantages as to the stability of trifluralin are inherent to the use of hydrobromic acid solution which is made possible and economically advantageous owing to the process of the invention. It may in fact be postulated that the treatment by hydrobromic acid avoids the formation of di-alkyl amines which are present at least partially also in the organic trifluralin phase and which in turn may react with nitrogen oxides which are present in the atmosphere to give nitrosamines derivatives. In order to verify the above hypothesis the following tests were carried out.

EXAMPLE 5

In these experimental tests, the crude trifluralin use was derived from the amination reaction according to equation I, shown hereinbefore, between di-n-propylamine (DPA) and 4-trifluoromethyl-2,6-dinitro-chlorobenzene (DN-Cl) in the presence of an aqueous solution of sodium hydroxide.

A portion of the trifluralin was used as such, whereas a second portion was subjected to repeated crystallization to obtain a pure product.

Both portions were separately treated for 3 hours at 90° C. under stirring with 10% by weight, referred to the weight of trifluralin, of an aqueous solution of 30% wt (tests 2 and 6) and respectively 37% wt (tests 3 and 7) of hydrochloric acid and with an amount of 30% wt, with respect to trifluralin, of an aqueous 30% wt HBr solution (tests 4 and 8).

At the end of the treatment the trifluralin product was separated by decantation from the aqueous acidic solution and washed with an aqueous solution of sodium bicarbonate at 60°–70° C. to neutralize the pH. According to tests 3 and 7 the treatment with fresh 37% wt HCl was repeated twice. The thus obtained refined product was analysed by FID gas chromatography.

The results of the analysis are summarized in Table III shown hereinafter.

TABLE III

| Test No. | Treatment | % wt/wt DN-Cl | % wt/wt DN-Br |
|---|---|---|---|
| 1 | crude trifluralin | n.d. | n.d. |
| 2 | crude trifluralin + 10% HCl 30% | 0.197 | n.d. |
| 3. | crude trifluralin + 10% HCl 37% (twice) | 1.489 | n.d. |
| 4 | crude trifluralin + 30% HBr 30% | n.d. | n.d. |
| 5 | crystallized trifluralin | n.d. | n.d. |
| 6 | crystallized trifluralin + 10% HCl 30% | 0.279 | n.d. |
| 7 | crystallized trifluralin + 10% HCl 37% (twice) | 1.252 | n.d. |
| 8 | crystallized trifluralin + 30% HBr 30% | n.d. | n.d. | n.d. = not determined (lower than the sensitivity threshold of the FID detector)

In all the tests carried out by treatment of trifluralin with hydrochloric acid solution, there was found the presence in the refined trifluralin of significant amounts of the compound 4-trifluoromethyl-2,-6-dinitro-chlorobenzene (DN-Cl), while the same compound was not found in the unrefined trifluralin (test 1).

The corresponding bromo derivative (DN-Br) was not found in the trifluralin treated by hydrobromic acid solution.

It is believed that the formation of the above mentioned chloro derivative is accompanied by the formation of di-n-propylamine as a result of the reversal of the reaction (I) cited hereinbefore.

The process according to the invention is therefore advantageous with respect to both the quality of the refined trifluralin which is thereby obtained and to the economical cost of the process proper. In fact the possibility of re-using the hydrobromic acid solution for several recyclings makes profitable the use thereof and furthermore the possibility of regenerating by distillation the solution of hydrobromic acid which is spent after several recyclings, avoids the problems relating to the discharge of the effluents from the plant and reduces the consumption of hydrobromic acid to almost stoichiometric levels.

I claim:

1. An improved process for purifying crude trifluralin containing nitrosamines to reduce the level thereof to below at least 0.5 ppm, wherein crude trifluralin is treated by mixing under agitation with an aqueous solution of hydrobromic acid, wherein the improvements consists of adding to said aqueous solution an amount of sulfamic acid of from 0.1 to 3 g per liter of said aqueous hydrobromic acid solution and an amount of a bisulfite of an alkali metal corresponding to a content of sulphur dioxide of from 0.3 to 1.2 g/l of said aqueous solution.

2. Process according to claim 1, wherein the aqueous solution of hydrobromic acid has a concentration of from 15 to 50% by weight.

3. Process according to claim 2, wherein the acqueous solution of hydrobromic acid has a concentration of from 23 to 27% by weight.

4. Process according to claim 1, wherein the ratio between the aqueous solution of hydrobromic acid and the unrefined trifluralin is between 0.2 and 0.8 liters per kilogram.

5. Process according to claim 4, wherein the ratio between the aqueous solution of hydrobromic acid and the unrefined trifluralin is between 0.4 and 0.6 liters per kilogram.

6. Process according to claim 1, wherein the sulfamic acid is added in the form of an aqueous solution having a concentration of between 10% and 20% by weight, the amount of said sulfamic acid being from 0.4 to 0.7 g per liter of hydrobromic acid solution.

7. Process according to claim 1, wherein said bisulfite of alkali metal is sodium bisulfite and the added amount of sodium bisulfite corresponds to a content of sulfur dioxide from 0.5 to 0.8 g per liter of said hydrobromic acid solution.

8. Process according to claim 1, wherein the reaction of trifluralin with hydrobromic acid added with sulfamic acid and bisulfite of alkali metal is carried out at a temperature from 60° to 90° C. for a time of 10 minutes to 4 hours.

* * * * *

UNITED STATES PATENT AND TRADEMARK OFFICE
CERTIFICATE OF CORRECTION

PATENT NO. : 4,874,895

DATED : October 17, 1989

INVENTOR(S) : Graziello DONADELLO

It is certified that error appears in the above-identified patent and that said Letters Patent is hereby corrected as shown below:

On the title page, Item:

[19], Line 2, delete "Graziello" and substitute therefor -- Donadello--.

[75], Line 5, delete "Donadello Graziello" and substitute therefor --Graziello Donadello--.

[56], Line 15, delete "Palluca" and substitute therefor --Pallucca--.

Front Page, [57], Line 14, delete "sulphur" and substitute therefor --sulfur--.

Column 3, Line 23, delete "characterised" and substitute therefor --chacacterized--;

Column 3, Line 27, delete "bisulphite" and substitute therefor --bisulfite--;

Column 3, Line 38, delete "was" and substitute therefor --is-;

Column 3, Line 43, delete "bisulphite" and substitute therefor --bisulfite--;

UNITED STATES PATENT AND TRADEMARK OFFICE
CERTIFICATE OF CORRECTION

PATENT NO. : 4,874,895
DATED : October 17, 1989
INVENTOR(S) : Graziello DONADELLO It is certified that error appears in the above-identified patent and that said Letters Patent is hereby corrected as shown below:

Column 3, Line 44, delete "sulphur" and substitute therefor --sulfur--;

Column 3, Line 61, after "that" insert --of--.

Column 4, Line 7, delete "azetropic" and substitute therefor --azeotropic--;

Column 4, Line 25, delete "sulphamic" and substitute therefor --sulfamic--;

Column 4, Line 37, delete "sulphamic" and substitute therefor --sulfamic--.

Column 5, Line 50, delete "obtaining" and substitute therefor -- obtained--.

Column 7, Line 63, delete "use" and substitute therefor --used--.

Column 8, Line 17, delete "analysed" and substitute therefor --analyzed--.

UNITED STATES PATENT AND TRADEMARK OFFICE
CERTIFICATE OF CORRECTION

PATENT NO. : 4,874,895
DATED : October 17, 1989
INVENTOR(S) : Graziello DONADELLO It is certified that error appears in the above-identified patent and that said Letters Patent is hereby corrected as shown below:

Column 9, Line 4, delete "sulphur" and substitute therefor --sulfur--;

Column 9, Line 9, delete "acque-" and substitute therefor --aque---,.

Signed and Sealed this

Twenty-eighth Day of December, 1993

Attest:

BRUCE LEHMAN

*Attesting Officer*    *Commissioner of Patents and Trademarks*